United States Patent [19]

Campbell

[11] Patent Number: 5,434,293
[45] Date of Patent: Jul. 18, 1995

[54] ALKYLATION OF ALKYL SALICYLATE USING A LONG CHAIN CARBON FEED

[75] Inventor: Curtis B. Campbell, Hercules, Calif.

[73] Assignee: Chevron Chemical Company, San Ramon, Calif.

[21] Appl. No.: 172,544

[22] Filed: Dec. 23, 1993

[51] Int. Cl.$^6$ ............................................. C07C 69/88
[52] U.S. Cl. ........................................................ 560/71
[58] Field of Search ........................................... 560/71

[56] References Cited

U.S. PATENT DOCUMENTS

| | | | |
|---|---|---|---|
| 2,490,444 | 12/1949 | Kooijman et al. | 260/521 |
| 4,810,398 | 3/1989 | Van Kruchten et al. | 252/40 |
| 5,225,588 | 7/1993 | Senaratne et al. | 560/71 |

FOREIGN PATENT DOCUMENTS

| | | |
|---|---|---|
| 2542732 | 9/1984 | France . |
| 269619 | 7/1989 | Germany . |
| 272065 | 9/1989 | Germany . |
| 54-160335 | 6/1978 | Japan . |
| 2097417 | 11/1982 | United Kingdom . |

OTHER PUBLICATIONS

Chemical Abst. 73:3663 1970.
Chem. Abst. 90:6111 1978.
Chem. Abst. 112:138761 1989.
Croxall et al, "Organic Reactions with Boron Fluoride. VII. The Rearrangement of Isoporpyl Salicylate and the Condensation of Propylene with Salicylic Acid," *J. Am. Chem. Soc.*, 56, 2054–2055 (1934).
Croxall et al, "Organic Reactions with Boron Fluoride XI. The Condensation of Propylene with m- and p-Hydroxybenzoic Acids," *J. Am. Chem. Soc.*, 57, 1549–1551 (1935).
Derwent Abstract No. 89-357182/49 1989.
Derwent Abstract No. 90-067884/10 1990.
Derwent Abstract No. 84-265358/43 1984.
Derwent Abstract No. 08382C/05 1983.
Meyer, et al, "Uber die Alkylierung Aromatischer Verbindungen," *Monatsh.*, 53 and 54, 721–52 (1929) (and Chem Abstract, vol. 24, pp. 346–347 (1930)).

*Primary Examiner*—Paul J. Killos
*Attorney, Agent, or Firm*—L. S. Squires; W. K. Turner

[57] ABSTRACT

Disclosed is a method for alkylating alkyl salicylate using a solid acidic alkylation catalyst and approximately equimolar amounts of alkyl salicylate and alkylating feedstock.

16 Claims, No Drawings

ALKYLATION OF ALKYL SALICYLATE USING A LONG CHAIN CARBON FEED

BACKGROUND OF THE INVENTION

1. Field of the Invention

This invention is directed to alkylation of an alkyl salicylate using a long chain carbon feed (e.g., a $C_5$–$C_{50}$ olefin or alcohol) to obtain products having a variety of uses, including use as intermediates suitable for the preparation of overbased lubricating oil additives.

2. State of the Art

Alkylation of alkyl salicylates (e.g., methyl salicylate) is known in the art. However, to effect alkylation, a liquid, gaseous or solid strong acid catalyst, such as sulfuric acid, methane sulfonic acid, molten $SbCl_2$—HCl, $BF_3$, $SnCl_4$ or an acid ion exchange resin, in combination with an alkylating feedstock and an excess of alkyl salicylate relative to the feedstock or in combination with alkyl salicylate and an excess of alkylating feedstock relative to the salicylate is typically employed in the art. Such processes are disclosed, for example, in Deutsche Patentschrifts DD 269 619 and DD 272,065, U.S. Pat. No. 5,225,588 and Japanese Patent Application No. 54/160335.

The processes disclosed in the art, however, suffer from many disadvantages. First, a combination of washing steps and/or severe stripping of the resulting crude alkylation product must be done to remove excess alkyl salicylate or excess alkylation feed, particularly long chain alkylation feed, as well as any liquid acid catalyst or dissolved gaseous acid catalyst which may have been used. However, excess alkyl salicylate or excess alkylation feed is typically employed to ensure conversion to the alkylated alkyl salicylate and, despite the resulting disadvantages of recovery, stripping of the excess alkyl salicylate or excess alkylation feed from the reaction product and recycling this excess is a necessary step from an economical point of view.

Second, the art discloses alkylation using only low carbon number alkylation feeds, for example, propylene, octene, tetradecene, styrene, isopropanol and methyl-t-butyl ether. German Patentschrift DD 269,619, for example, discloses alkylation of a salicylic acid derivative in the presence of an acidic ion exchanger as the catalyst using a linear or branched $C_2$–$C_{14}$ olefin (optionally aryl-substituted).

The use of higher carbon number alkylation feeds is not as efficient as alkylation with lower carbon number feeds because such feeds are typically less reactive and methods of compensating for the reduced reactivity are necessary such as the use of an excess of alkyl salicylate relative to the alkylation feed.

In view of the above, methods for alkylation of alkyl salicylate using a long chain carbon feed (e.g., $C_{15}$–$C_{50}$ olefin or alcohol) wherein the process does not require an excess of alkyl salicylate or an excess of alkylation feed would be desirable from both a processing point of view and an economic point of view. It would also be desirable that such methods be conducive to the efficient manufacture of alkylated alkyl salicylate.

SUMMARY OF THE INVENTION

This invention is based, in part, on the discovery that alkyl salicylate may be alkylated with a long chain carbon feed by using a solid acidic alkylation catalyst preferably having a Hammett value ($H_o$) of less than about $-2$ (more negative).

In addition to permitting the use of long chain carbon feeds, this invention is further based, in part, on the discovery that the methods described herein provide for substantially alkylated alkyl salicylate while using substantially equimolar amounts of alkyl salicylate and alkylation feedstock during reaction. In turn, because the product is substantially alkylated alkyl salicylate and further because substantially equimolar amounts of reagents are employed, little unreacted alkyl salicylate or carbon feed remains after reaction completion and, accordingly, the stripping and recycling steps of the prior art are either greatly reduced or eliminated.

This invention is also based, in part, on the fact that since a solid acidic alkylation catalyst is employed, efficiencies in the manufacturing of alkylated alkyl salicylates are enhanced because the alkylated product is readily separated from the solid catalyst (e.g., by filtration techniques or other equivalent methods).

In view of the above, in one of its method aspects, this invention is directed to a method for alkylation of alkyl salicylate which method comprises:

(a) combining approximately equimolar amounts of a carbon feed comprising an olefin or an alcohol of about 15 to about 50 carbon atoms and an alkyl salicylate of the formula

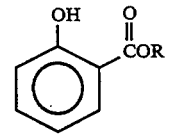

wherein R is an alkyl group of from 1 to 6 carbon atoms; and (b) alkylating said carbon feed onto said alkyl salicylate by combining the mixture produced in (a) above with a solid acidic alkylation catalyst under conditions sufficient to effect such alkylation.

In a preferred embodiment, the carbon feed is preferably from about 20 to 50 carbon atoms. More preferably, the carbon feed is a mixture of $C_{20}$–$C_{28}$ olefins and still more preferably a mixture of $C_{20}$–$C_{28}$ alpha olefins or a mixture of $C_{20}$–$C_{24}$ alpha olefins.

In another preferred embodiment, the product produced in (b) above is separated from the alkylation catalyst and optionally, but preferably, is subsequently stripped under relatively mild conditions, e.g., at temperatures of from about 130° C. to about 240° C. and pressures of from about 0.5 to about 10 millimeters (ram) of mercury, it being preferred, however, to maintain stripping temperatures as low as possible. In one example, stripping is conducted at a temperature of about 130° C. and a pressure of from about 1 to 5 mm of mercury. In another example, stripping is conducted at a temperature of from about 185° C. to about 200° C., and then at a temperature between about 230° C. and 240° C. while maintaining a pressure of less than about 10 mm of mercury.

In still another preferred embodiment, the solid acidic alkylation catalyst has a Hammett value ($H_o$) of less than $-2$ (i.e., more negative).

The alkylated alkyl salicylates prepared by the methods described above are useful intermediates in the preparation of overbased products which, when used as lubricating oil detergent additives, exhibit excellent water tolerance, thermal stability, detergency, compatibility and oxidation performance in finished lubricating oil formulations. See, for example, U.S. Ser. No. 08/173,192 filed concurrently herewith and entitled "OVERBASED ALKYLATED ALKYL SALICYLATES" which application is incorporated herein by reference in its entirety.

Alternatively, the alkyl salicylates can be subjected to hydrolysis to provide salicylic acid which, in turn, can be overbased to provide useful detergent additives. See, for example, British Patent No. GB 2 097 417 A, and U.S. Pat. No. 4,810,398 both of which are incorporated herein by reference in their entirety.

DETAILED DESCRIPTION OF THE PREFERRED EMBODIMENTS

This invention is directed to novel methods for alkylation of alkyl salicylate with a long chain carbon feed using a solid acidic alkylation catalyst preferably having a Hammett ($H_o$) value of less than $-2$. Surprisingly, when such solid acidic alkylation catalysts are employed, the alkylation procedure does not require the use of an excess amount of alkyl salicylate or carbon feed but, rather, essentially equimolar amounts of carbon feed and alkyl salicylate are employed. Moreover, the resulting product is substantially alkylated. The use of the solid acidic alkylation catalyst also permits facile separation of the catalyst from the product.

However, prior to discussing this invention in detail, the following terms will first be defined:

Definitions

The term "alkyl salicylates" refers to compounds of the formula:

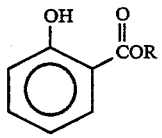

wherein R is an alkyl group of from 1 to 6 carbon atoms. Preferably, R is an alkyl group of from 1 to 3 carbon atoms and most preferably R is methyl.

The term "alkylated alkyl salicylate" refers to alkyl salicylates which have been alkylated with a long chain carbon feed which alkylated products can be represented by the formula:

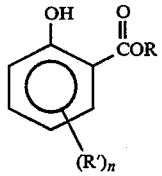

where R is as defined above; R' is an alkyl group of from about 15 to 50 carbon atoms; and n is an integer of from 1 to 2 but preferably 1.

The term "carbon feed" or "carbon feedstock" refers to feeds suitable for use in alkylating alkyl salicylate in the presence of a solid acidic alkylation catalyst. Suitable feeds include, by way of example, olefins and alcohols. Mixtures of suitable materials can also be used, e.g., a mixture of olefins, a mixture of alcohols, a mixture of olefins and alcohols, and the like.

In the methods of this invention, the carbon feed is preferably an alcohol or olefin having from about 15 to about 50 carbon atoms and more preferably from about 20 to about 50 carbon atoms. In a particularly preferred embodiment, the carbon feed is a mixture of $C_{20}$–$C_{28}$ olefins and still more preferably a mixture of $C_{20}$–$C_{28}$ alpha olefins or a mixture of $C_{20}$–$C_{24}$ alpha olefins.

The term "substantially straight-chain alkyl group" means an alkyl group which is attached to the benzene ring of alkyl salicylate through a secondary, tertiary or quaternary carbon atom and which contains minimal branching in the remainder of the carbon atoms of the alkyl group (i.e., less than 20% of the remaining carbon atoms are tertiary and/or quaternary carbon atoms in the molecular structure of the alkyl group).

Preferably, the substantially straight-chain alkyl group contains less than 15% tertiary and/or quaternary carbon atoms in the remainder of the alkyl group; more preferably, less than 10%; still more preferably, less than 5%; and most preferably, the substantially straight-chain alkyl group contains no tertiary or quaternary carbon atoms in the remainder of the alkyl group.

Substantially straight-chain alkylated alkyl salicylates are preferably prepared by reacting alkyl salicylate with either a substantially straight-chain olefin or alcohol.

The term "olefin" refers to any hydrocarbon containing a monoolefin group ($>C=C<$) within its structure.

The term "alcohol" refers to any alkane compounds containing a monohydroxyl substituent (—OH) within its structure.

The term "alpha olefin" refers to hydrocarbons containing a monoolefin group at one of the terminal portions of the hydrocarbon so as to terminate in a $CH_2=CH-$ group. Examples of alpha olefins include 1-hexadecene [($CH_2=CH(CH_2)_{13}CH_3$)], 1-octadecene [($CH_2=CH(CH_2)_{15}CH_3$)] and the like.

The term "substantially straight-chain alpha olefin" means an alpha olefin which contains minimal branching (i.e., less than 20% of the carbon atoms are tertiary and/or quaternary carbon atoms) in the molecular structure.

The term "substantially straight-chain alcohol" means an alcohol which contains minimal branching (i.e., less than 20% of the carbon atoms are tertiary and/or quaternary carbon atoms) in the molecular structure. In this regard, alcohols having hydroxyl substitution at the 1, 2, or 3 positions at either terminus of the alkane are referred to as "terminal alcohols". Alcohols having hydroxyl substitution at positions other than the 1, 2, or 3 positions of either terminus of the alkane chain are referred to as "internal alcohols".

Methodology

In the methods of this invention, the alkylated alkyl salicylate products are prepared by alkylation of alkyl salicylate with a carbon feed having from about 15 to about 50 carbon atoms in the presence of a solid acidic alkylation catalyst under conditions wherein the carbon feed alkylates the salicylate.

Alkyl salicylates are well known in the art and are either commercially available or can be prepared by conventional synthetic methods. For example, methyl salicylate is available from Aldrich Chemical Company, Milwaukee, Wis., USA and the methyl ester can be readily exchange using conventional transesterification techniques to provide for other alkyl salicylates.

Alkyl salicylate is alkylated by reacting therewith an approximate equimolar amount of a carbon feed having from about 15 to about 50 carbon atoms in the presence of a solid acidic alkylation catalyst.

Suitable solid acidic alkylation catalysts include, by way of example, any acid catalyst which is solid under the alkylation conditions employed, is essentially insoluble in the reaction medium (i.e., solubility of less than about 0.5 g/liter of reaction solution), and capable of effecting alkylation of alkyl salicylate with a long chain carbon feed. Preferred solid acidic alkylation catalysts have a Hammett value ($H_o$) of less than about $-2$ (i.e., more negative) and preferably have suitable porosity to permit effective contact between the catalyst and the reagents so that other methods of ensuring effect contact during reaction can be avoided.

Suitable solid acidic catalysts are known in the art and include, by way of example, fluorocarbonsulfonic acid polymer heterogeneous acid catalyst (available from DuPont, Wilmington, Del. under the tradename of NAFION®), sulfonic acid resin catalysts (available from Rohm & Haas, Philadelphia, Pa. under the tradename of AMBERLYST®, e.g., AMBERLYST® 15 and AMBERLYST® 36) and the like.

The catalyst is generally used in an amount between about 5 and about 30 weight percent relative to the carbon feed, and preferably in an amount of about 20 weight percent relative to the carbon feed.

Approximate equimolar amounts of carbon feed as used in this reaction preferably include molar ratios of carbon feed to alkyl salicylate of from about 0.9:1 to about 1.1:1 and more preferably from about 0.95:1 to about 1.05:1.

The reaction is preferably conducted either neat or in an inert diluent under conditions suitable for alkylating the alkyl salicylate with the carbon feed. Suitable diluents include, by way of example, chlorobenzene, chlorinated hydrocarbons having a boiling point of greater than about 150° C., paraffins, lubricating oil, and the like.

The reaction is preferably conducted at a temperature of from about 100° C. to about 180° C., and more preferably at from about 120° C. to about 140° C. and can be conducted either in a batch or a continuous process. The specific temperature or temperature range employed during alkylation will depend upon various factors, including the specific catalyst employed in the alkylation reaction. Optimization of the temperature based on such factors is well within the skill of the art.

When a batch process is employed, requisite amounts of the reagents and diluent, if employed, are combined into a reaction vessel and the reaction is preferably maintained at a temperature as recited above. Reaction pressures are not critical and the reaction pressure can be atmospheric, sub-atmospheric and super-atmospheric pressure and the reaction is conducted for a period of time to effect alkylation. Preferably, alkylation is effected over a period of from about 10 to about 100 hours and more preferably from about 12 to about 50 hours. The specific time employed during batch alkylation will depend upon various factors, including the specific catalyst employed in the alkylation reaction and the reaction temperature. Optimization of reaction time based on the particular catalyst and reaction temperature employed is well within the skill of the art.

In a continuous process, the solid acidic alkylation catalyst can be placed in a catalyst bed in a continuous alkylation unit and a stream of carbon feed and alkyl salicylate passed through the unit under conditions to effect alkylation. Preferably, the reaction parameters are selected to provide for from about 5 to about 100 hours of catalyst contact time and a Liquid Hourly Space Velocity (LHSV) of from about 0.03 to about 5 $hr^{-1}$. As before, reaction pressures are not critical and reaction pressures can be sub-atmospheric, atmospheric and super-atmospheric. The specific catalyst contact time and LHSV employed during continuous alkylation will depend upon various factors, including the specific catalyst employed in the alkylation reaction and the reaction temperature. Optimization of catalyst contact time and LHSV based on the particular catalyst and reaction temperature employed is well within the skill of the art.

In either event, after reaction completion, the product is optionally but preferably stripped to remove any diluent, unreacted carbon feed, and the like. Because the methods of this invention provide for effective alkylation, stripping can be conducted under relatively mild conditions, i.e., at temperatures of from about 130° C. to about 240° C. and pressures of from about 0.5 to about 10 mm of mercury.

By the process of this invention, the alkyl salicylate can be alkylated in any of the positions, e.g., either ortho or para to the hydroxyl group, or ortho or para to the ester group on the benzene ring. Generally, a mixture of alkylation products will result including some dialkylation of the alkyl salicylate. The particular mixture of alkylation products that results will depend on the specific reaction conditions of the reaction. Preferably, dialkylation is minimized to less than about 5 weight percent of the product.

In a preferred embodiment, a predominantly straight chain olefin or alcohol fraction containing some branching in the molecular structure at the double bond or the hydroxyl functionality may be used, such as the olefin structures depicted below:

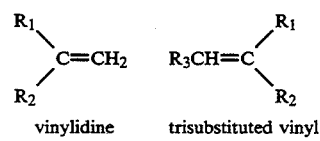

vinylidine          trisubstituted vinyl wherein $R_1$, $R_2$ and $R_3$ form the remainder of the carbon feed, e.g., a $C_{15}$–$C_{50}$ olefin.

Suitable predominantly straight chain olefins and alcohols are those wherein about 75 to 100 number percent and preferably about 85 to 100 number percent of the individual carbon atoms of the olefin or alcohol are either primary ($CH_3$—) or secondary (—$CH_2$—). Included in the terms primary or secondary are alpha olefins (—CH=$CH_2$) and internal olefins (—CH=CH—). In the converse, such predominantly straight chain olefins and alcohols can contain from 9 to about 25 number percent although preferably from 0 to about 15 number percent of tertiary carbon atoms. Included within the term tertiary are trisubstituted vinyl groups (>C=CH—) and vinylidine (>C=$CH_2$).

Predominantly straight chain olefin fractions are commercially available products such as $C_{18}$–$C_{30}$ olefins, available from Ethyl Corporation, Baton Rouge, La. and $C_{24}$–$C_{28}$ and $C_{20}$–$C_{28}$ olefin fractions, available from Chevron Chemical Corporation, San Ramon, Calif., USA. Straight chain olefins, containing less than about 5 mole percent branched olefins, are available from Shell Chemical Company, Houston, Tex., USA.

In a more preferred embodiment, the olefin is an alpha olefin comprising a substantially straight-chain alkyl group having at least about 15 carbon atoms and more preferably between about 20 and 28 carbon atoms. In a particularly preferred embodiment, the alpha olefin comprises a substantially straight-chain alkyl group having between 20 and 24 carbon atoms.

In an optional embodiment, after formation of the alkylated alkyl salicylate in the manner described above, the recovered product can be subjected to conventional hydrolysis well documented in the art to provide for the alkylated salicylic acid.

Utility

The alkylated methyl salicylates described herein are useful as intermediates in the preparation of lubricating oil additives. Specifically, these compounds are useful intermediates in the preparation of overbased products which, when used as lubricating oil detergent additives, exhibit excellent water tolerance, thermal stability, detergency, compatibility and oxidation performance in finished lubricating oil formulations. See, for example, U.S. Ser. No. 08/173,192 filed concurrently herewith as Attorney Docket No. 005950-369 and entitled "OVERBASED ALKYLATED ALKYL SALICYLATES" which application is incorporated herein by reference in its entirety.

Alternatively, the methyl salicylates can be subjected to hydrolysis to provide salicylic acid which can be overbased to provide useful detergent additives.

The invention will be illustrated in greater detail by the following specific examples. It is understood that these examples are given by way of illustration only and are not meant to limit the disclosure of the claims to follow.

EXAMPLES

Comparative Example A—Preparation of Alkylated Methyl Salicylate Using an Excess of Methyl Salicylate The purpose of this example is to determine the effect on product composition when an excess of methyl salicylate relative to the carbon feed is employed during alkylation.

Specifically, methyl salicylate (from Aldrich Chemical Company, Milwaukee, Wis., USA) was alkylated with a $C_{20}$–$C_{24}$ olefin carbon feed at a molar ratio of 5:1 of methyl salicylate to carbon feed. In this example, 1802.6 grams of a $C_{20}$–$C_{24}$ olefin fraction (available from Chevron Chemical Corporation, San Francisco, Calif.), was charged to a 5 liter, four-neck oven dry flask. 2457.5 grams of methyl salicylate followed by 591.3 grams of AMBERLYST ®36 sulfonic acid resin (available from Rohm and Haas, Philadelphia, Pa., USA) were next charged to the flask. The flask was then equipped with a stirrer, temperature probe with controller, reflux condensor and a nitrogen blanket.

The reaction mixture was heated to a temperature of 125° C. over a period of 50 minutes and held at that temperature for approximately 48 hours. After 48 hours, about 94.2% conversion of the methyl salicylate to alkyl methyl salicylate had occurred. The reaction mixture was cooled with stirring overnight to a temperature of about 50° C.

The crude alkyl methyl salicylate was removed from the reaction flask by using a gas dispersion tube and pulling it into a four liter flask under vacuum. The catalyst remained in the reaction flask. Product remaining on the catalyst was removed by rinsing the contents of the flask with approximately 400 ml portions of toluene while stirring, followed by pulling the toluene and crude product into a two liter flask through a gas dispersion tube under vacuum. This rinsing/pulling procedure was repeated additional three times. The toluene recovered in this procedure was stripped on a rotovap at a temperature of approximately 95° C. to 100° C. under vacuum (~25 mm of Hg vacuum) and the resulting stripped product was combined with the recovered crude alkylated methyl salicylate.

The combined crude alkylated methyl salicylate was then stripped at a temperature of about 130° C. at a pressure of approximately 1 to 10 mm of mercury. Further stripping was conducted at a temperature of about 185° C. to 191° C. at a pressure of approximately 1 to 10 mm of mercury. Product analysis indicated that about 94.7 weight percent of the methyl salicylate was alkylated.

Example 1

Preparation of Alkyl Methyl Salicylate Using 1:1 Molar Ratio of Olefin to Methyl Salicylate Methyl salicylate commercially obtained from Aldrich Chemical Company, Milwaukee, Wis., USA was alkylated using a long chain carbon feed. In this example, 6 17.9 grams (2 moles) of a $C_{20}$–$C_{24}$ alpha olefin fraction (available from Chevron Chemical Corporation, San Francisco, Calif.), was charged to a 2 liter, three-neck oven dry flask. 304.3 grams (2 moles) of methyl salicylate, followed by 150 grams of AMBERLYST ®36 (a solid acidic sulfonic acid resin catalyst commercially available from Rohm & Haas, Philadelphia, Pa., USA), were next charged to the flask. The flask was then equipped with a stirrer, temperature probe with controller, reflux condensor and a nitrogen blanket.

The reaction mixture was heated to a temperature of 135° C. over a period of 25 minutes and held at that temperature for approximately 61 hours while periodically removing aliquots to check reaction completion. After 61 hours, the recovered product was analyzed for its components which analysis is reported in Table I below:

TABLE I

| COMPONENTS IN RECOVERED ALKYLATED METHYL SALICYLATE | |
|---|---|
| COMPONENT | WEIGHT PERCENT |
| salicylic acid | 1.5% |
| olefin | 6.5% |
| alkyl methyl salicylate | 87.5% |
| methyl salicylate | 4.5% |

The product was filtered through a sintered glass filter. The filtered alkyl methyl salicylate was heated to a temperature of 210° C. over a period of about 45 minutes and then stripped under vacuum of about 1 to 10 mm of Hg was applied. These stripping conditions were maintained for about 30 minutes. The stripped product was next cooled to 150° C. and the vacuum broken with a nitrogen stream. 739.9 grams of product was recovered. Analysis of this product is set forth in Table II below:

TABLE II

COMPONENTS IN RECOVERED AND STRIPPED ALKYLATED METHYL SALICYLATE

| COMPONENT | WEIGHT PERCENT |
| --- | --- |
| salicylic acid | 0.1% |
| olefin | 4.7% |
| alkyl methyl salicylate | 95.2% |

The above data demonstrates that the crude product obtained by the methods of this invention contains substantially alkylated methyl salicylate. The above data further demonstrates that after mild stripping, the product of Example 1 contains substantially the same amount of alkylated methyl salicylate as compared to the stripped product of Comparative Example A. The above data still further demonstrates that a product of >95 weight percent alkylated methyl salicylate can be further obtained by use of the methods of this invention coupled with relative mild stripping conditions.

Insofar as Example 1 employs equimolar amounts of methyl salicylate and carbon feed, whereas Comparative Example A employs a 5:1 ratio of these components, these results establish that the methods of this invention do not require the use of excess methyl salicylate to achieve substantial amounts of alkylated methyl salicylate.

While the invention has been described in terms of various preferred embodiments, the skilled artisan will appreciate that various modifications, substitutions, omissions, and changes may be made without departing from the spirit thereof. Accordingly, it is intended that the scope of this invention be limited solely by the scope of the following claims, including equivalents thereof.

What is claimed is:

1. A method for alkylation of alkyl salicylate which method comprises:

(a) combining approximately equimolar amounts of a carbon feed comprising an olefin or an alcohol of about 15 to about 50 carbon atoms and an alkyl salicylate of the formula

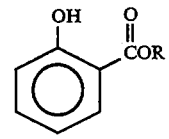

wherein R is an alkyl group of from 1 to 6 carbon atoms; and (b) alkylating said carbon feed onto said alkyl salicylate by combining the mixture produced in (a) above with a solid acidic alkylation catalyst under conditions sufficient to effect such alkylation.

2. The method according to claim 1 wherein the long chain carbon feed is a mixture of $C_{20}$–$C_{28}$ olefin.

3. The method according to claim 2 wherein the long chain carbon feed is a mixture of $C_{20}$–$C_{28}$ alpha olefin.

4. The method according to claim 3 wherein the long chain carbon feed is a mixture of $C_{20}$–$C_{24}$ alpha olefin.

5. The method according to claim 1 wherein said long chain carbon feed is a substantially straight chain olefin or alcohol.

6. The method according to claim 5 wherein said long chain carbon feed is a substantially straight chain olefin.

7. The method according to claim 1 wherein the methyl salicylate is reacted with the mixture of $C_{20}$–$C_{28}$ olefin in the presence of a solid acidic alkylation catalyst at a temperature of from about 100° C. to about 180° C.

8. The method according to claim 7 wherein said alkylation is conducted in a continuous process.

9. The method according to claim 1 wherein said method is a batch method.

10. The method according to claim 1 wherein said solid acidic alkylation catalyst is employed in an amount of from about 5 to about 30 weight percent relative to the carbon feed.

11. The method according to claim 10 wherein said solid acidic alkylation catalyst has a Hammett value of less than $-2$.

12. The method according to claim 11 wherein said solid acidic alkylation catalyst is a fluorocarbonsulfonic acid polymer heterogeneous acid catalyst.

13. The method according to claim 11 wherein said solid acidic alkylation catalyst is a sulfonic acid resin catalyst.

14. The method according to claim 1 wherein R is an alkyl group of from 1 to 3 carbon atoms.

15. The method according to claim 14 wherein R is methyl.

16. The method according to claim 1 which further comprises treating the product produced in (b) to hydrolysis under conditions sufficient to provide for alkylated salicylic acid.

* * * * *